US008317784B2

(12) United States Patent
Choe et al.

(10) Patent No.: US 8,317,784 B2
(45) Date of Patent: Nov. 27, 2012

(54) MAGNETIC SWITCHING DEVICE

(75) Inventors: William Choe, Highlands Ranch, CO (US); Sang Won Yoon, Ann Arbor, MI (US)

(73) Assignee: Cardiac Lead Technologies, LLC, Bethesda, MD (US)

( * ) Notice: Subject to any disclaimer, the term of this patent is extended or adjusted under 35 U.S.C. 154(b) by 0 days.

(21) Appl. No.: 12/840,747

(22) Filed: Jul. 21, 2010

(65) Prior Publication Data
US 2011/0060330 A1    Mar. 10, 2011

Related U.S. Application Data

(60) Provisional application No. 61/227,351, filed on Jul. 21, 2009.

(51) Int. Cl.
*A61B 18/12* (2006.01)
(52) U.S. Cl. .......................................................... 606/34
(58) Field of Classification Search ............... 607/9–38, 607/2, 5, 60, 63; 128/899; 606/32–50
See application file for complete search history.

(56) References Cited

U.S. PATENT DOCUMENTS

| | | | | |
|---|---|---|---|---|
| 5,518,001 | A * | 5/1996 | Snell | 600/510 |
| 6,618,617 | B2 * | 9/2003 | Chen et al. | 607/5 |
| 6,694,184 | B2 * | 2/2004 | Cappa et al. | 607/2 |
| 6,771,155 | B2 | 8/2004 | Asa | |
| 2002/0095187 | A1 * | 7/2002 | Thompson et al. | 607/9 |
| 2003/0050676 | A1 * | 3/2003 | Hubelbank et al. | 607/60 |
| 2005/0096703 | A1 | 5/2005 | Sanders | |
| 2007/0233200 | A1 | 10/2007 | Maschke | |
| 2009/0149906 | A1 * | 6/2009 | Ameri et al. | 607/9 |
| 2009/0163980 | A1 * | 6/2009 | Stevenson | 607/63 |
| 2010/0125191 | A1 * | 5/2010 | Sahin | 600/411 |

OTHER PUBLICATIONS

Cavicchi, Elizabeth. "Series and Parallel Experimenting With Electromagnets" in "Volta and the Histroy of Electricity". 2002, 1999 Conference Proceedings, 387-407, see pp. 388-394.*
International Search Report and Written Opinion dated Sep. 16, 2010, directed to counterpart application No. PCT/US2010/042767. (9 pages).

* cited by examiner

*Primary Examiner* — Michael Peffley
*Assistant Examiner* — Ronald Hupczey, Jr.
(74) *Attorney, Agent, or Firm* — Venable LLP; Henry J. Daley; Ryan M. Flandro

(57) ABSTRACT

A magnetic switching device includes an electromagnetic component adapted to be arranged proximate to an exterior surface of an object having a magnetically-switchable device therein and a control circuit electrically connected to the electromagnetic component. The electromagnetic component is constructed to generate a magnetic field of sufficient strength and orientation to engage a switch in the magnetically-switchable device. The invention further includes an electrocautery system, including an electrocautery device, a control circuit electrically connected to the electrocautery device, and an electromagnetic component electrically connected to the control circuit. The electromagnetic component is adapted to be arranged proximate to an exterior surface of an object having a magnetically-switchable device therein. Operation of the electrocautery device causes the electromagnetic component to generate a magnetic field of sufficient strength to engage a switch in the magnetically-switchable device.

22 Claims, 11 Drawing Sheets

| TYPE | INSULATOR/AIR CORE | METAL/FERROMAGNETIC CORE |
|---|---|---|
| AMPLITUDE OF MAGNETIC FIELD | OK | OK |
| DIRECTION OF MAGNETIC FIELD | BIT WORSE CONTROL | BETTER CONTROL |
| WEIGHT | LIGHT | HEAVY |
| EXPENSE | LOW | BIT HIGHER |
| FABRICATION CONVENIENCE | EASIER | HARDER |
| WIRE | ANY WIRE | SHOULD BE COATED W/ INSULATOR |

MAGNETIC SWITCHING DEVICE

CROSS-REFERENCE TO RELATED APPLICATION

This application claims priority to U.S. Provisional Application No. 61/227,351 filed on Jul. 21, 2009, the entire contents of which are hereby incorporated by reference.

BACKGROUND

1. Field of Invention

This application relates to magnetic switching devices and systems, and more particularly to magnetic switching devices and systems for controlling embedded electrical devices.

2. Discussion of Related Art

Currently in the United States, there are thousands of patients implanted with electrical devices, for example, but not limited to, pacemakers and/or implantable cardioverter-defibrillators (ICDs). A pacemaker, also called an artificial pacemaker, is a device which uses electrical impulses, delivered by electrodes contacting the heart muscles, to regulate the beating of the heart. An ICD is a small battery-powered electrical impulse generator which is implanted in patients who are at risk of sudden cardiac death due to ventricular fibrillation and ventricular tachycardia. The ICD is programmed to detect cardiac arrhythmias and correct it by delivering a jolt of electricity.

Many patients with such electrical devices will require non-cardiac surgery or procedures at some point during their lifetime which may interfere with their electrical devices. Non-cardiac surgery may include the use of electrocautery during surgery, lithotripsy, for treatment of kidney stones, the use of a transcutaneous electrical nerve stimulation (TENS) device, or radiation therapy in the treatment of cancer. This presents a serious problem, as many electrical devices are sensitive to electromagnetic interference (EMI) from other electrical devices used during surgery. Consequently, many implantable devices are designed with a magnetically operable switch to shut off the device or switch it to a "backup mode" when a magnetic field is applied. For example, a patient's pacemaker exposed to EMI may malfunction. Similarly, a patient's ICD may mischaracterize EMI as ventricular fibrillation (VF) and may deliver a shock to the patient. VF is a condition in which there is an uncoordinated contraction of the cardiac muscle of the ventricles in the heart, making them quiver rather than contract properly.

Several methods have been adopted to avoid the influence of EMI on an imbedded electrical device during surgery. However, these methods have some serious limitations. For example, one solution in avoiding EMI is to reprogram the magnetically-switchable device. However, reprogramming generally requires a technically skilled person to be present to reprogram each device, making reprogramming an expensive option.

Another known solution is to place a magnet over a magnetically-switchable, electrical device to inactivate or place the device in a backup mode. The type of magnet used is usually a large permanent magnet, such as a donut magnet. Needless to say, it is difficult to position and to ensure that the magnet stay in place during surgery. Shifting of the magnet during an operation could reactivate the magnetically-switchable, electrical device, for example the pacemaker or ICD, and put the patient at risk.

SUMMARY

There thus remains a need for devices and/or systems to facilitate control of embedded electrical devices. One embodiment of the present invention relates to a magnetic switching device that includes an electromagnetic component adapted to be arranged proximate to an exterior surface of an object comprising a magnetically-switchable device therein; and a control circuit electrically connected to the electromagnetic component, wherein the electromagnetic component is constructed to generate a magnetic field of sufficient strength to engage a switch in the magnetically-switchable device.

Another embodiment of the present invention relates to an electrocautery system that includes an electrocautery device; a control circuit electrically connected to the electrocautery device; and an electromagnetic component electrically connected to the control circuit, wherein the electromagnetic component is adapted to be arranged proximate to an exterior surface of an object comprising a magnetically-switchable device therein, and wherein operation of the electrocautery device causes the electromagnetic component to generate a magnetic field of sufficient strength to engage a switch in the magnetically-switchable device.

This summary is provided merely to introduce certain concepts and not to identify any key or essential features of the claimed subject matter. Further features and advantages of embodiments of the invention, as well as the structure and operation of various embodiments of the invention, are described in detail below with reference to the accompanying drawings.

DETAILED DESCRIPTION

Figure 1A:
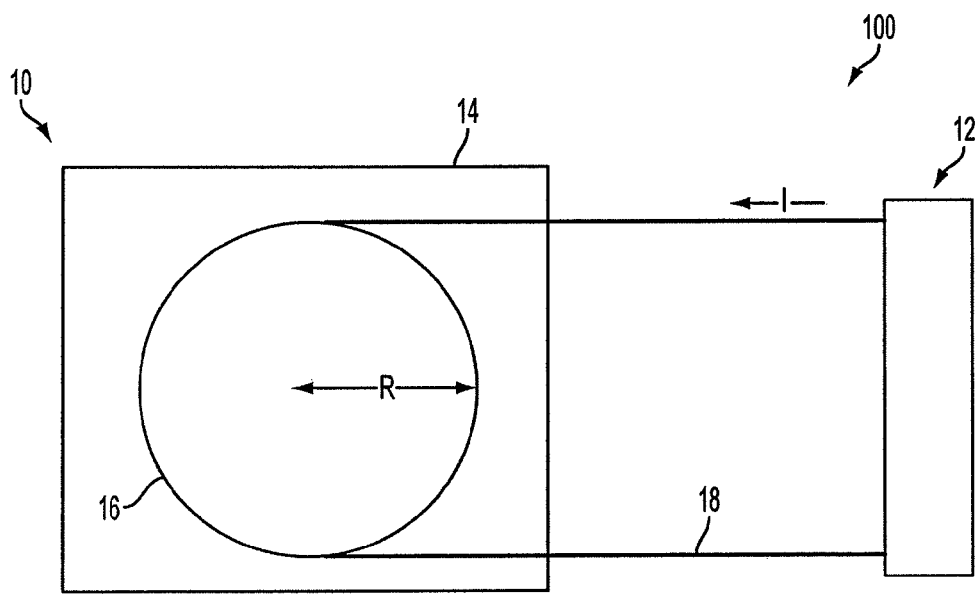
FIG. 1A is a schematic illustration showing a top view of a magnetic switching device, in accordance with at least some embodiments of the present invention.

FIG. 1A is schematic illustration of a top view of a magnetic switching device 100, in accordance with at least some embodiments of the present invention. The magnetic switching device 100 may include an electromagnetic component 10 in electrical connection to a control circuit 12. The electromagnetic component 10 may include a patch 14 adapted to be arranged proximate to an exterior surface of an object 20 (see FIG. 2A), for example a human medical patient, having an embedded magnetically-switchable device 22 (see FIG. 2A), for example a pacemaker or ICD. However, the general concepts of the current invention are not limited to only pacemakers and ICDs implanted in people. Other types of magnetically-switchable devices could be implanted in the patient or even some non-human object. When activated, the control circuit 12 delivers a current I to the electromagnetic component 10 which, in turn, generates a magnetic field B (see FIG. 2B) of sufficient strength and orientation to engage a switch (not shown) in the magnetically-switchable device 22 of the object 20. According to one embodiment, the electromagnetic component 10 will generate a magnetic field of approximately 0.1 to 45 Gauss when activated.

According to another embodiment, the magnetic field B generated by the electromagnetic component 10 may cause the magnetically-switchable device 22, here a pacemaker, to go VOO, i.e. to revert into back-up mode. According to a further embodiment, the magnetic field B generated by the electromagnetic component 10 may cause the magnetically-switchable device 22, here an ICD, to turn of its sensing function and to go into a backup pacing mode. In either embodiment, deactivation of the electromagnetic component 10, which stops the generation of the magnetic field B, can re-engage the switch of the magnetically-switchable device 22, causing the magnetically-switchable device 22 to revert back to its original settings and to resume normal operation.

According to one embodiment, the patch 14 may be an adhesive patch adapted to be affixed to the exterior surface of the object 20. In that case, the adhesive patch may prevent the electromagnetic component 10 from accidentally shifting during surgery potentially moving the electromagnetic component 10 out of the necessary proximity to the magnetically-switchable device 22, thus failing to switch the magnetically-switchable device 22 to a backup mode or some other desired mode of operation during EMI. For these same reasons, the patch width may include additional tolerance to compensate for error during surgery. Alternatively, other fastening devices may be used, such as straps, clips, stickers, suction devices and/or medical tape. The patch 14 may further be reusable or disposable.

According to another embodiment, the electromagnetic component 10 further includes a core 16 that is coupled to or positioned on the patch 14. A wire 18, for example an enamel-covered wire, may be wound around the core 16 to produce an electromagnetic coil 11 (see FIG. 1B). The wire 18 may provide the electrical connection of the electromagnetic component 10 to the control circuit 12. The wire 18 may be in the range of approximately 0.3 to 1.3 millimeters in diameter, for example. According to another embodiment, the wire thickness may range from approximately 0.25 centimeters to 0.6 centimeters.

According to a further embodiment of the current invention, the core 16 may be embodied as a plastic donut, a plastic cylinder, a metal cylinder and/or a metal donut. The embodiment of the metal cylinder core 16, for example a ferromagnetic core, may provide a maximum magnetic field, however weight may become a consideration. For example, it may be advisable to limit the weight of the core 16 to approximately eight pounds.

According to one embodiment, the electromagnetic component 10 may include a heat absorber and/or heat dissipater (not shown) to absorb/dissipate the heat generated by the coil 11. The heat absorber may be embodied as a single-piece insulating layer, a multi-piece insulating layer, or passive/active heat dissipation system, such as a layer of gel. The heat absorber may be coupled to or positioned on the patch 14.

Figure 1B:
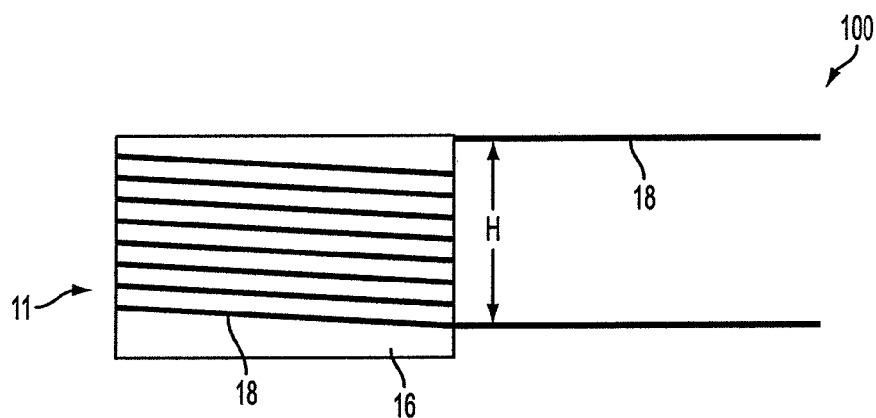
FIG. 1B is a side view of the electromagnetic coil of the magnetic switching device of FIG. 1A.

FIG. 1B is a side view of the electromagnetic coil 11 of the magnetic switching device 100 of FIG. 1A. Generally, an electromagnetic coil 11 may refer to a coil of wire that is formed to produce a magnetic field B when current I flows through the coil. One loop of wire 18 is generally referred to as a "turn," and a coil 11 consists of one or more turns. In other words, the coil 11 may be accomplished with a minimum of one loop or turn. As seen in FIG. 1B, the wire 18 is wound around the core 16 eight times to produce eight turns. As such, the control circuit 12 may send a current I through the wire 18 to the coil 11 of the electromagnetic component 10 to generate the magnetic field B over the magnetically-switchable device 22 embedded in the object 20.

According to one embodiment, the control circuit 12 may transmit approximately five Amperes of current I to the electromagnetic component 10 via the wire 18. Five Amperes is used only as an example of a current I. The current I could be more than five Amperes or it could be less. A smaller current I may reduce the heat generated by the coil 11. In this embodiment, the five Amperes of current I through a wire 18, where the wire 18 is approximately 0.5 millimeters in diameter, may generate approximately 12 Watts of power. The 12 Watts of power may generate approximately 172 calories/minute.

According to another embodiment, the portion of the patch 14 affixed or positioned in close proximity to the exterior surface of the object 20 may be dimensioned as 15 centimeters by 15 centimeters. The coil 11 may have a radius R of approximately 7 centimeters and a height H of approximately 3 centimeters. The current I transmitted from the control circuit 12 to the electromagnetic component 10 may be approximately five Amperes (A).

Figure 2A:
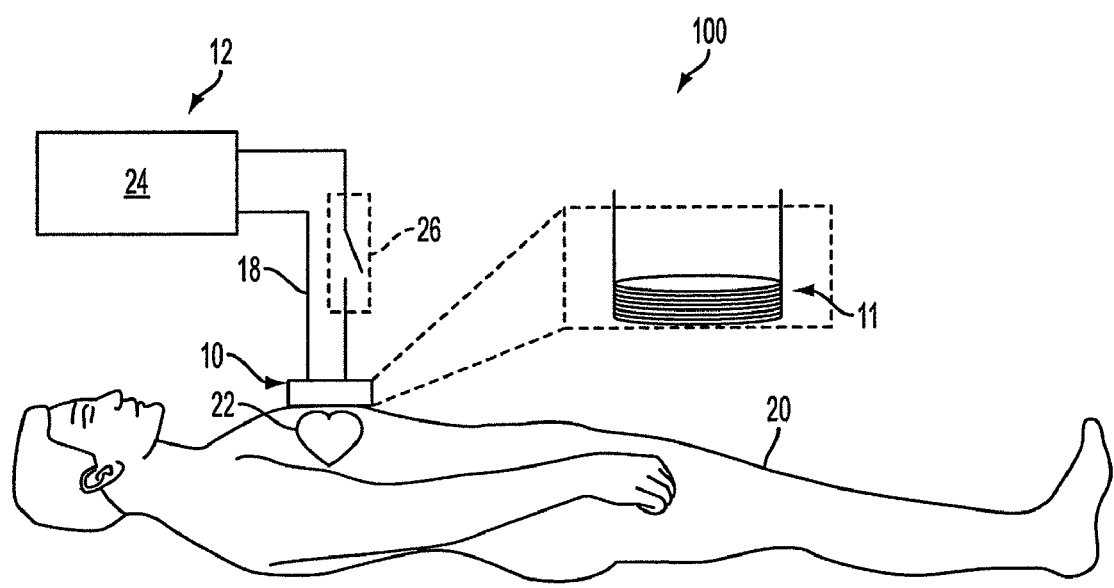
FIG. 2A is a schematic diagram of the magnetic switching device during a "power off stage," in accordance with some embodiments of the present invention.

FIG. 2A is a schematic diagram of the magnetic switching device 100 during a "power off stage," in accordance with some embodiments of the present invention. As shown in FIG. 2A, the electromagnetic component 10 has been positioned on the exterior surface of an object 20, for example a medical patient, above the object's magnetically-switchable device 22. Here, the control circuit 12, also called a "electrocautery generator," may comprise a DC or AC power supply 24 electrically connected to the electromagnetic component 10 via a wire 18 having a switch 26, also called an "electrocautery pen." In other embodiments, the switch 26 may be an "on/off" switch, a foot petal and/or any other activation device. In the embodiment of FIG. 2A, the switch 26 is open, thus preventing the power supply 24 from supplying a current I to the coil 11 of the electromagnetic component 10. The coil 11 of the electromagnetic component 10, therefore, cannot generate a magnetic field B. This may be referred to as the "power off stage."

Figure 2B:
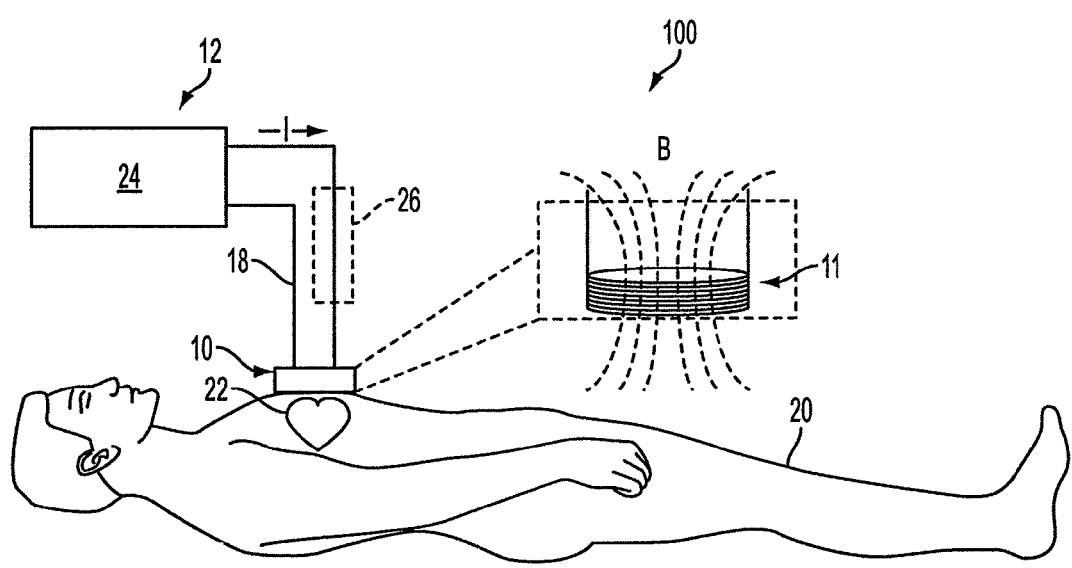
FIG. 2B is a schematic diagram of the magnetic switching device during a "power on stage," in accordance with some embodiments of the present invention.

FIG. 2B is a schematic diagram of the magnetic switching device 100 during a "power on stage," in accordance with some embodiments of the present invention. In FIG. 2B, the switch 26 is closed, thus transmitting current I from the power supply 24 to the coil 11 of the electromagnetic patch 10 which then generates a magnetic field B of sufficient strength to engage the switch in the embedded magnetically-switchable device 22. This may be referred to as the "power on stage."

According to one embodiment, approximately eight Gauss may be required to effectuate a backup mode on the magnetically-switchable device 22. Furthermore, the coil 11 may be adapted to generate a magnetic field B that is perpendicular to the skin surface of the object 20. The coil radius R may be sized to accommodate magnetically-switchable devices 22 of different types, sizes and shapes. The coil radius R may be, for example, but not limited to, between 4.2 and 9.5 centimeters. The coil 11 may be embodied as a dot magnet with a highly concentrated and directed magnetic field B. Alternatively, the coil 11 may be provided with a slightly larger radius R for additional tolerance to compensate for the spacing between the coil 11 and the magnetically-switchable device 22 embedded in the object 20. Additional tolerance may be desirable when the center of the magnetically-switchable device 22 is unknown. Furthermore, additional tolerance may compensate for any shifting of the magnetically-switchable device 22 within object 20 due to body movement during surgery.

According to another embodiment, the current I is approximately five Amperes, the skin thickness of the object 20 is approximately 5 centimeters, and the magnetic field B is at least eight Gauss during operation. The skin thickness of the object 20 may be used to determine the distance of the magnetically-switchable device 22 from the coil 11 of the electromagnetic component 10. This distance may be calculated by adding the skin thickness of the object 20, or medical patient, and the patch 14 thickness, where the patch 14 is directly affixed to the exterior surface, or skin, of the object 20.

Figure 3:
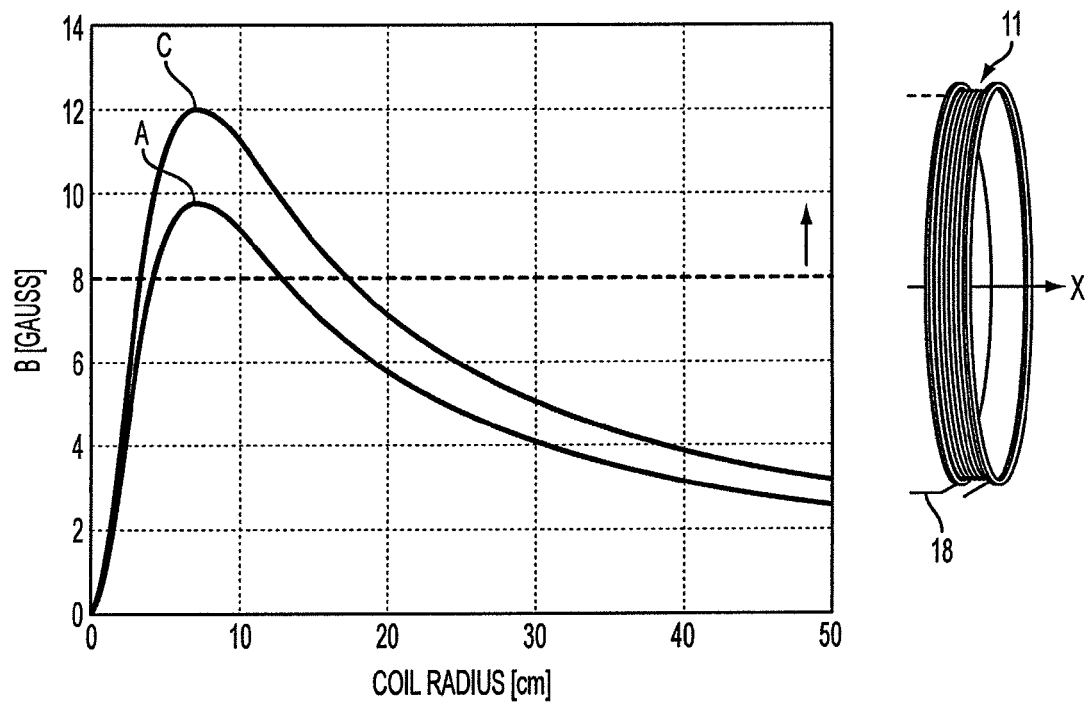
FIG. 3 is a graphical diagram showing simulation results for the strength of the magnetic field delivered at the magnetically-switchable device based on the number of wire turns of the electromagnetic coil, in accordance with some embodiments of the present invention.

FIG. 3 is a graphical diagram showing simulation results for the strength of the magnetic field B delivered at the magnetically-switchable device 22 based on the number of wire turns of the electromagnetic coil 11, in accordance with some embodiments of the present invention. As described above, the wire 18 may be wound around the circumference of the core 16 a pre-determined number of times to produce an electromagnetic coil 11 adapted to generate an appropriate magnetic field B during the power on stage. The pre-determined number of turns, for example, but not limited to, may be between 30 and 50 turns of wire 18. FIG. 3 depicts a graph of the simulation results of the magnetic switching device 100 based on varying numbers of turns of the wire 18.

The embodiment of FIG. 3, assumes that an ideal circular coil 11 is used, including, for example, an air or cylindrical/donut fixture that does not generate any magnetic field other than that which is generated by the coil 11. For example, the coil 11 may include a plastic cylinder, as seen in FIGS. 1A, 1B, 2A and 2B. Such an ideal circular coil 11 is depicted to the right of the graph in FIG. 3. The embodiment assumes that the skin thickness of the object 20 is approximately five centimeters. Skin thickness may be used to calculate the depth of the magnetically-switchable device 22 in the object 20, which may in turn be used to calculate the strength of the magnetic field B experienced at the magnetically-switchable device 22. The embodiment further assumes that the current through the wire 18 is approximately five Amperes. In this embodiment, the electromagnetic component 10 requires a minimum magnetic field B of eight Gauss to generate a magnetic field B of sufficient strength to engage the switch (not shown) of the magnetically-switchable device 22. A coil 11 having 40 turns of wire and a coil radius of approximately eight centimeters would produce a magnetic field B of approximately 9.6 Gauss, as shown in Example A. Meanwhile, a coil 11 having 50 turns of wire and a coil radius of approximately seven centimeters would produce a magnetic field of B of approximately 12 Gauss, as shown in Example C. This embodiment shows that the strength of the magnetic field B at the magnetically-switchable device 22 is proportional to the number wire turns and depends on the coil radius. The coil 11 is not limited to 40 or 50 turns of the wire 18, other embodiments, for example 30 turns of wire, are also possible.

Figure 4:
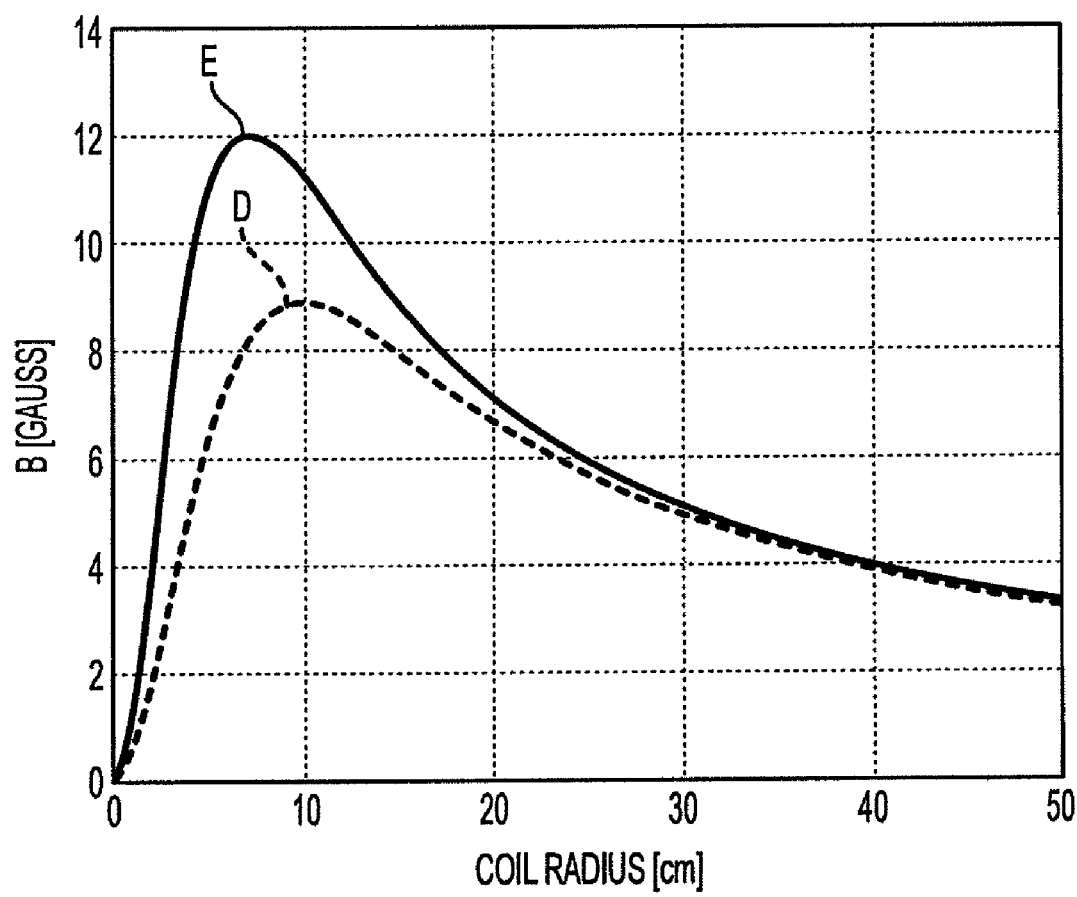
FIG. 4 is a graphical diagram showing simulation results for the strength of the magnetic field delivered at the magnetically-switchable device based on the skin thickness of the object, in accordance with some embodiments of the present invention.

FIG. 4 is a graphical diagram showing simulation results for the strength of the magnetic field B delivered at the magnetically-switchable device 22 based on the skin thickness of the object 20, in accordance with some embodiments of the present invention. As described above, an object's 20 skin thickness may be used to determine the depth of the magnetically-switchable device 22 within the object 20 and, thus, the strength of the magnetic field B at that depth. According to one embodiment, the depth of the magnetically-switchable device 22 will not exceed a depth of five inches from the skin surface.

In Example D of FIG. 4, an object's 20, or patient's, skin thickness is approximately seven centimeters. Under Example D, an approximately 9.5 centimeter coil radius will generate a magnetic field B of approximately 8.75 Gauss. In Example E, an object's 20, or patient's, skin thickness is approximately five centimeters. Under Example E, an approximately seven centimeter coil radius will produce a magnetic field B of approximately 12 Gauss. Likewise, when an object's 20, or patient's, skin thickness is one centimeter, an approximately 4.2 centimeter coil radius will produce the maximum magnetic field B at the given skin thickness (not shown). FIG. 4 demonstrates the need to optimize the radius of the coil 11 depending on depth of the magnetically-switching device 22 within the object.

Figure 5:
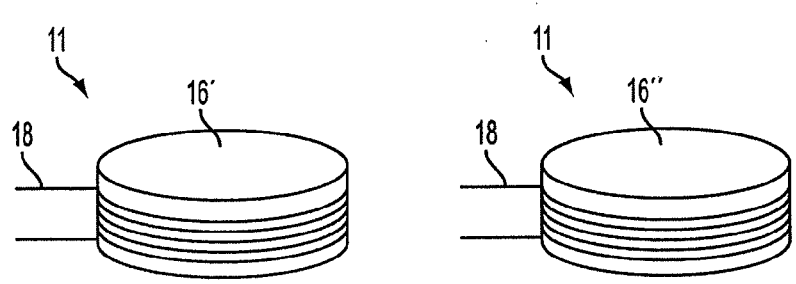
FIG. 5 is a chart comparing various characteristics of the magnetic core of the magnetic switching device, in accordance with some embodiments of the present invention.

FIG. 5 is a chart comparing various characteristics of the core 16 of the magnetic switching device 100, in accordance with some embodiments of the present invention. According to one embodiment, the coil 11 may include an insulator or air core 16', as depicted to the top left of the chart. An insulator core refers to an insert that is positioned within the coil 11 and that is constructed from plastic or another insulating material. An air core simply refers to the coil 11 having a non-existent hollow core, i.e. it uses open spaces between the loops of the coil 11 for air. An insulator/air core 16' is light-weight, low-cost, easy to fabricate and produces an acceptable amplitude of the magnetic field B. Any wire 18 may be used with the insulator/air core 16'. However, the insulator/air core 16' does not allow for precise control of the direction of the magnetic field B and produces a smaller amplitude of magnetic field B than would the metal/ferromagnetic core 16" in FIG. 5. The example shown in FIG. 5 is a cylinder, however other shapes, such as a donut, may be used.

According to another embodiment, the coil 11 may include a metal/ferromagnetic core 16", as depicted to the top right of the chart. The metal/ferromagnetic core 16" may be constructed from iron, nickel, or any other ferromagnetic material. The metal/ferromagnetic core 16" has an acceptable amplitude of the magnetic field B and has a better control of the direction of the magnetic field B than the insulator/air core 16' Specifically, the metal/ferromagnetic core 16" is better able to concentrate or focus the magnetic field B towards the magnetically-switchable device 22 embedded in the object 20. However, the metal/ferromagnetic core 16" is heavy, more expensive and harder to fabricate. Further, the metal/ferromagnetic core 16" must be used in conjunction with a wire 18 which is coated with an insulator or, alternatively, the surface of the core 16" itself must be coated with an insulator.

Figure 6:
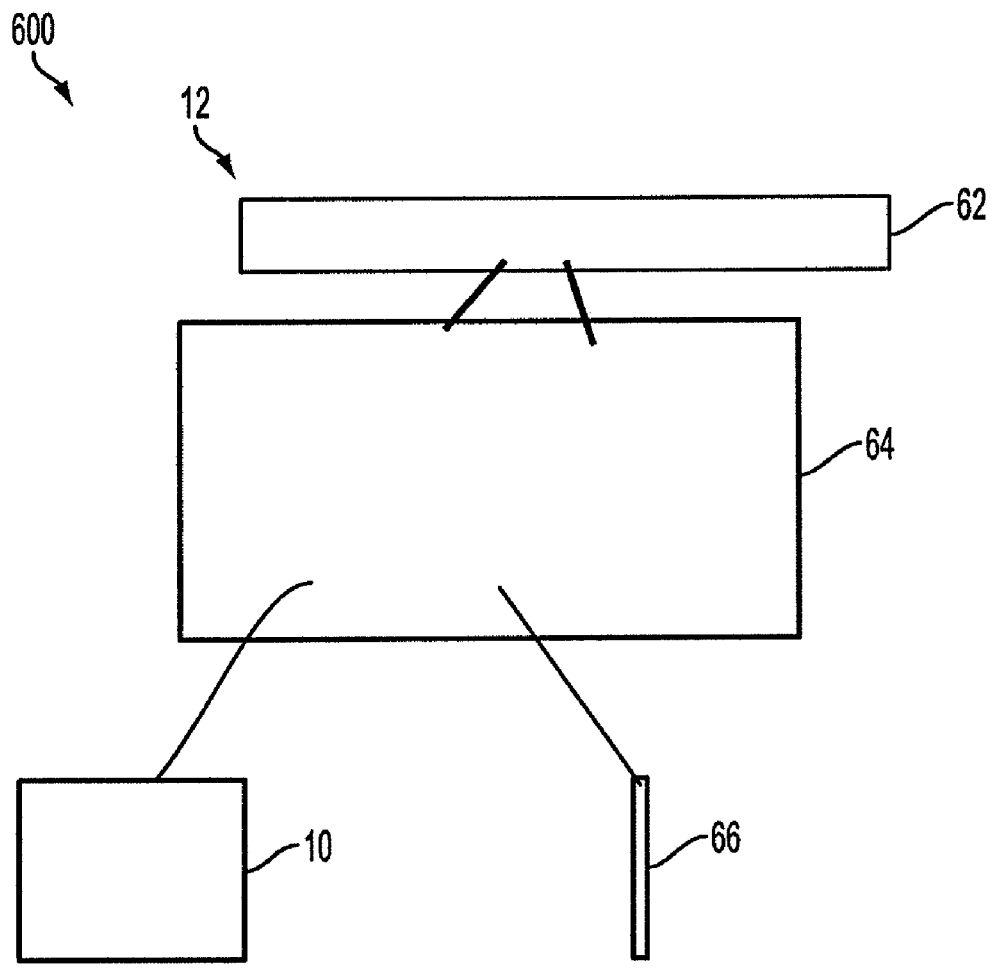
FIG. 6 is a schematic illustration of a top view of an electrocautery system, in accordance with some embodiments of the present invention.

FIG. 6 is a schematic illustration of a top view of an electrocautery system 600, in accordance with some embodiments of the present invention. In this embodiment, a control circuit 12, including a power unit 62 and switch box 64, is in electrical connection with both an electromagnetic component 10 and an electrocautery device 66. The electrocautery device 66 may be any device used for electrocauterization, i.e. the process of destroying tissue using heat conduction from a metal probe heated by an electric current, and may be referred to as an electrocautery pen. In this embodiment, when in use, the electrocautery device 66 triggers an input into the switch box 64, which switches on the power unit 62 to send an output current Ito the electromagnetic component 10. As with the prior embodiments, the electromagnetic component 10 is adapted to be arranged proximate to an exterior surface of an object 20 having an embedded magnetically-switchable device 22 (see FIGS. 2A and 2B). When current I is transferred from the power unit 62 to the electromagnetic component 10, the electromagnetic component 10 is adapted to generate a magnetic field B of sufficient strength to engage a switch in the magnetically-switchable device 22.

This embodiment prevents EMI from interfering with the object's 20 magnetically-switchable device 22 during surgery. Examples of non-cardiac surgery may include the use of electrocautery during surgery, lithotripsy, the use of a TENS device, or radiation therapy. Each time the surgeon uses the electrocautery device 66, the control circuit 12 activates the electromagnetic component 10 to generate a magnetic field B over the magnetically-switchable device 22, thus halting or modifying the normal operation of the magnetically-switchable device 22 and preventing a disruption or malfunction due to EMI. This is again shown in FIG. 7, in which a simplified circuit diagram of the electrocautery system is shown.

Figure 7:
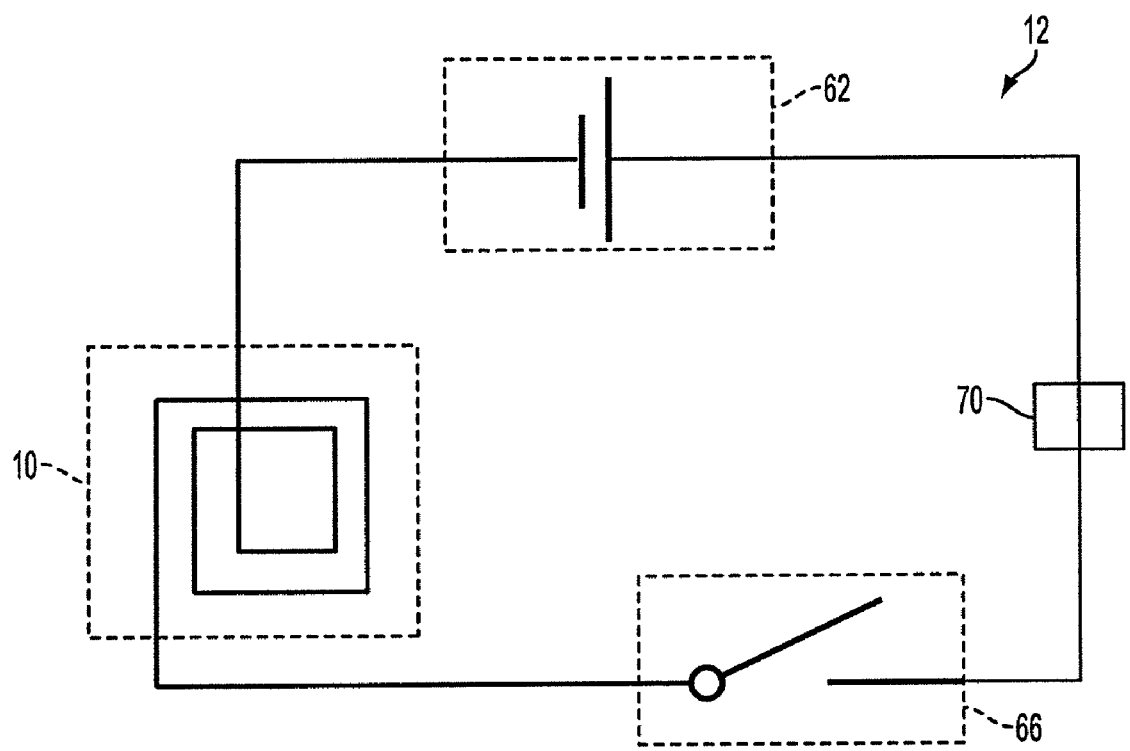
FIG. 7 is a circuit diagram of the electrocautery system, in accordance with some embodiments of the present invention.

As seen in FIG. 7, control circuit 12, including a power source 62, is electrically connected to both an electromagnetic component 10 and an electrocautery device 66. When the electrocautery device 66 is in use during an operation, the circuit loop closes, thus connecting the control circuit 20, the electromagnetic component 10 and the electrocautery device 66 in series. This connection enables the power source 62 to transmit a current I to the electromagnetic component 10 for generation of a magnetic field B. When the electrocautery device 66 is not in use, the loop remains open and no current I may pass to the electromagnetic component 10.

According to one embodiment, the control circuit 12 may optionally include a protective circuit 70 to prevent electrical shock generated while turning the electrocautery device 66 on and off. The protective circuit 70 may be positioned between the power source 62 and the electrocautery device 66 and/or switch 26. Alternatively, the protective circuit may be positioned between the electrocautery device 66 and/or switch 26 and the electromagnetic component 10.

According to one embodiment, the electrocautery system 600 may include a lock-out at ten seconds or some other programmable period of time to prevent an accidental reprogramming of an ICD. Some ICD models reprogram if a magnet is applied for more than several seconds. This embodiment may be able to control the duration of the magnet application in such a case or leave this setting off if reprogramming is not an obstacle. In addition, it is possible that the electromagnet may generate too much heat and such a lock-out system may set a duration of the electromagnetism to prevent this.

According to another embodiment, either the magnetic switching device 100 or the electrocautery system 600 may include a lighting device or LED device to show a user, for example a surgeon, that the electromagnetic component 10 is in use.

According to a further embodiment, the electrocautery device 66 may be directly plugged into the control circuit 12 of the electrocautery system 600. Since the electrocautery device 66 may act as the electrocautery system 600 on/off switch, according to one embodiment the electrocautery device 66 should plug into the electrocautery system 600 prior to operation.

Figure 8:
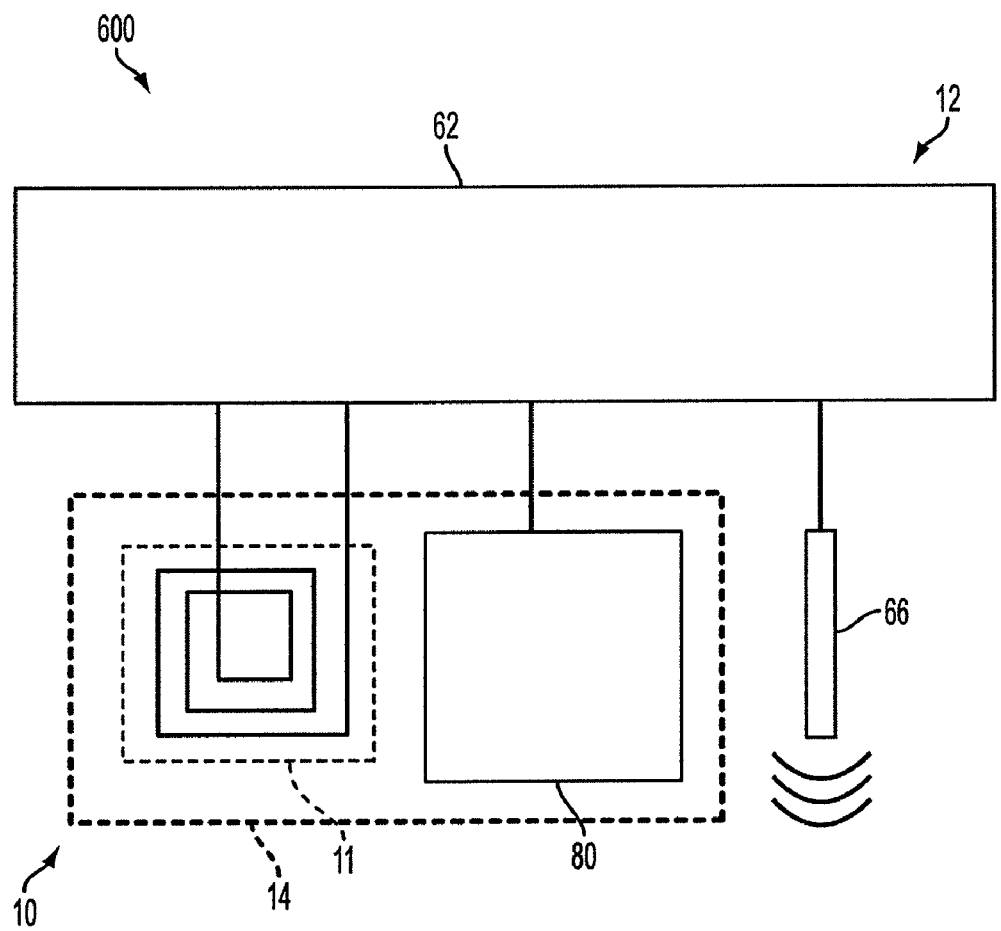
FIG. 8 is a schematic diagram of the electrocautery system, in accordance with some embodiments of the present invention.

FIG. 8 is a schematic diagram of the electrocautery system 600, in accordance with some embodiments of the present invention. In this embodiment, a ground patch 80 may be coupled to the patch 14 to ground the object 20, i.e. the patient during surgery. The ground patch 80 may be a separate pad connected to a bypass, which may be positioned on an extremity of the object 20 and away from the patch 14 of the electromagnetic component 10. The ground patch 80, according to one embodiment, need not be incorporated with the bypass.

Figure 9:
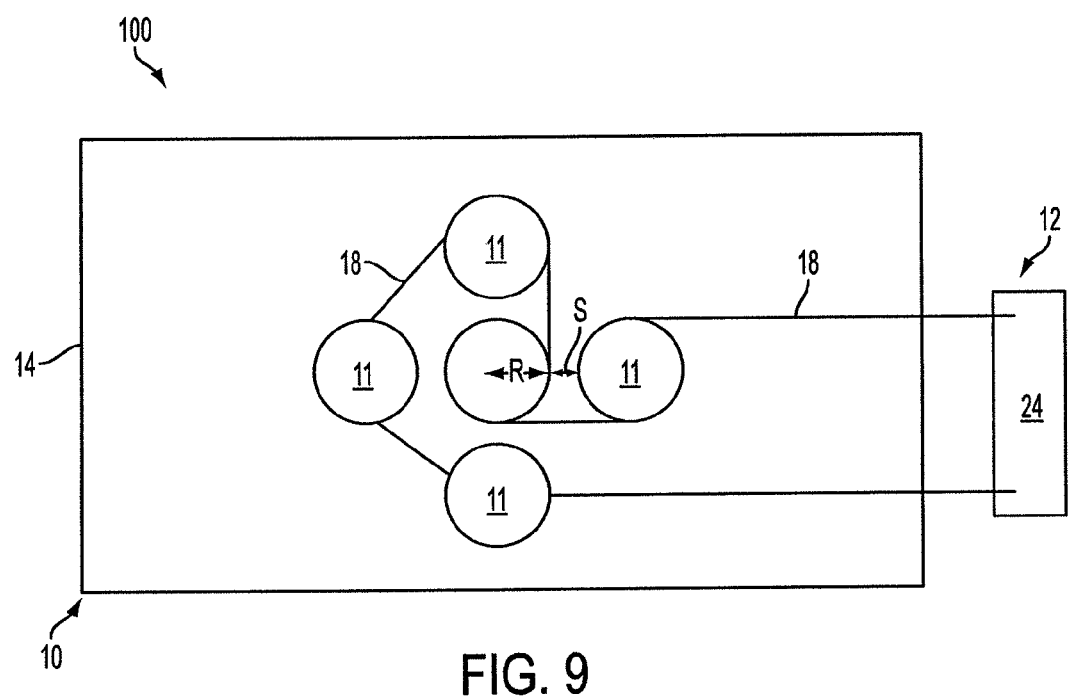
FIG. 9 is a schematic diagram of the magnetic switching device having a plurality of coils connected in series to a power source, in accordance with at least some embodiments of the present invention.

FIG. 9 is a schematic diagram of the magnetic switching device 100 having a plurality of coils 11 connected in series to a power source 24, in accordance with at least some embodiments of the present invention. In this embodiment, five coils 11 are connected via wire 18 to power source 24. The coils 11 may each be coupled to and/or positioned on the patch 14 and may have, for example, a radius R of 4.2 centimeters. The coils 11 may be positioned at a distance S from one another, which may be, for example, 0.2 centimeters apart. The plurality of coils 11 may concentrate a stronger and more directed magnetic field B on the magnetically-switchable device 22. The plurality of coils 11 may increase the tolerance to compensate in the case where the center of the magnetically-switchable device 22 is unknown or where the magnetically-switchable device 22 shifts within object 20 due to body movement during surgery.

Figure 10:
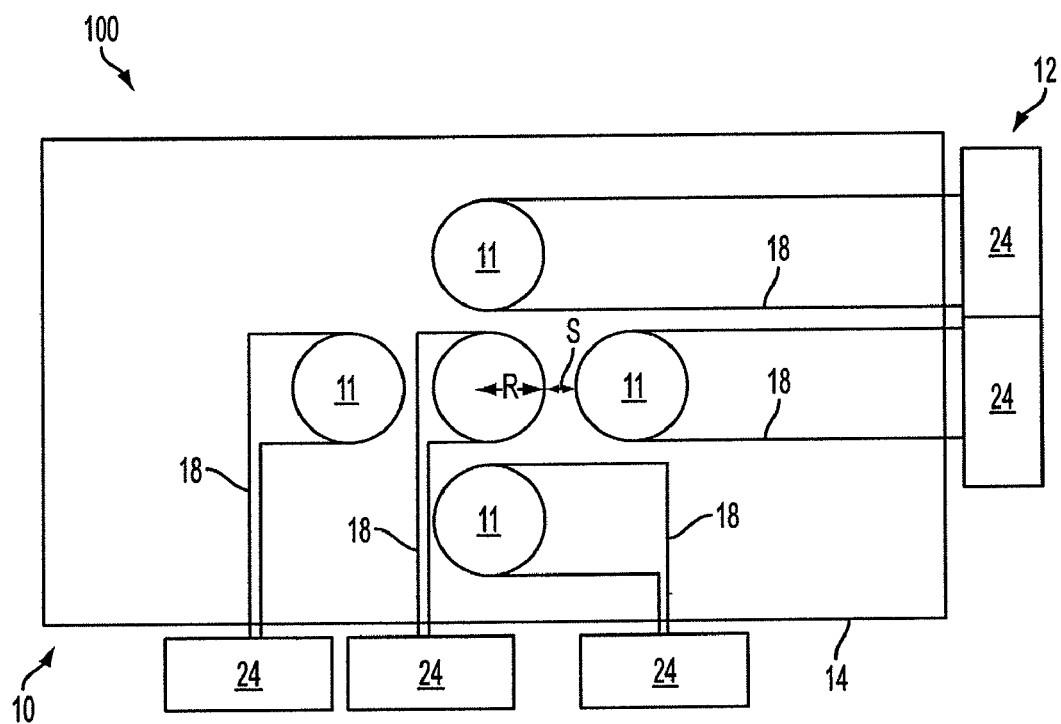
FIG. 10 is a schematic diagram of the magnetic switching device having a plurality of coils connected in parallel to a plurality of power sources, in accordance with at least some embodiments of the present invention.

FIG. 10 is a schematic diagram of the magnetic switching device 100 having a plurality of coils 11 connected in parallel to a plurality of power sources 24, in accordance with at least some embodiments of the present invention. In this embodiment, five coils 11 are positioned on or coupled to the patch 14 of the electromagnetic component 10. Each coil 11 is connected to a separate power source 24. Each coil 11 may further be connected to a separate trigger and/or switch 26. The power sources 24 may optionally be external power sources to the system. A connecting module (not shown) may be used to correlate the operation of each coil 11 of the magnetic switching device 100. Here again, the coils 11 may have a radius R, for example 4.2 centimeters, and may be positioned at a distance S from one another, for example 0.2 centimeters. The plurality of coils 11 may increase the tolerance to compensate in the case where the center of the magnetically-switchable device 22 is unknown or where the magnetically-switchable device 22 shifts within object 20 due to body movement during surgery.

According to a further embodiment, a hybrid system may be used (not shown). The hybrid system may use both an electromagnetic coil 11 and a permanent magnet to generate a magnetic field B of sufficient strength and orientation to engage a switch in the magnetically-switchable device 22 of the object 20. In this embodiment, a thinly sliced static or permanent magnet may be combined with an electromagnet coil 11 to produce a more powerful magnetic field B over the magnetically-switchable device 22. Meanwhile, the magnetic field B generated only by the static or permanent magnet may be smaller than eight Gauss so that it cannot turn on the the magnetically-switchable device 22 of the object 20, unless the coil 11 is activated. The permanent magnet may either be looped together with the electromagnet coil 11 using wire 18 or may be layered on top of the electromagnet coil 11. This embodiment may reduce the amount of electricity needed to effectively operate the electromagnetic component 10 of the magnetic switching device 100.

The present invention, in various embodiments, includes components, methods, processes, systems and/or apparatuses substantially as depicted and described herein, including various embodiments, subcombinations, and subsets thereof. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments to facilitate a description of some concepts of the current invention. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included descriptions of one or more embodiments and certain variations and modifications, other variations and modifications are within the scope of the invention, e.g., as may be within the skill and knowledge of those in the art, based upon teachings of the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. An electrocautery system, comprising:
   an electrocautery device;
   a control circuit electrically connected to the electrocautery device; and
   an electromagnet electrically connected to the control circuit,
   wherein the electromagnet is adapted to be arranged proximate to an exterior surface of an object comprising an implantable magnetically-switchable device therein,
   wherein the electromagnet comprises an electromagnetic coil having at least one turn,
   wherein operation of the electrocautery device causes the electromagnet to generate a magnetic field of sufficient strength to switch the magnetically-switchable device off or into back-up mode, and
   wherein the magnetic field generated by the electromagnet is between 0.1-45 Gauss.

2. The electrocautery system of claim 1, wherein the electromagnet comprises an adhesive patch adapted to be affixed to the exterior surface of the object.

3. The electrocautery system of claim 1, wherein the magnetically-switchable device comprises a pacemaker or an implantable cardioverter-defibrillator.

4. The electrocautery system of claim 1, wherein the electromagnet includes a lighting device adapted to indicate whether the electromagnet is generating the magnetic field.

5. The electrocautery system of claim 1, wherein the electrocautery device is adapted to trigger activation of the electromagnet during use.

6. The electrocautery system of claim 1, wherein the electromagnetic coil comprises a plurality of coils connected in series or in parallel to at least one power source.

7. The electrocautery system of claim 1, wherein the electromagnet is further constructed to generate a magnetic field of sufficient orientation to switch the magnetically-switchable device off or into back-up mode.

8. The electrocautery system of claim 1, wherein the electromagnetic coil defines a hollow space therein.

9. The electrocautery system of claim 1, wherein the magnetic field generated by the electromagnet is at least 8 Gauss.

10. The electrocautery system of claim 1, further comprising a lock-out connected to the control circuit that is configured to shut off the electromagnet after a predetermined period of time to prevent the magnetically-switchable device from automatically reprogramming.

11. The electrocautery system of claim 10, wherein the predetermined period of time is approximately 10 seconds.

12. An electrocautery system, comprising:
    an electrocautery device;
    a control circuit electrically connected to the electrocautery device; and
    an electromagnet electrically connected to the control circuit,
    wherein the electromagnet is adapted to be arranged proximate to an exterior surface of an object comprising an implantable magnetically-switchable device therein,
    wherein the electromagnet comprises an electromagnetic coil having at least one turn,
    wherein operation of the electrocautery device causes the electromagnet to generate a magnetic field of sufficient strength to switch the magnetically-switchable device off or into back-up mode, and
    wherein the electromagnet comprises an adhesive patch adapted to be affixed to the exterior surface of the object.

13. The electrocautery system of claim 12, wherein the magnetically-switchable device comprises a pacemaker or an implantable cardioverter-defibrillator.

14. The electrocautery system of claim 12, wherein the electromagnet includes a lighting device adapted to indicate whether the electromagnet is generating the magnetic field.

15. The electrocautery system of claim 12, wherein the magnetic field generated by the electromagnet is between 0.1-45 Gauss.

16. The electrocautery system of claim 12, wherein the electrocautery device is adapted to trigger activation of the electromagnet during use.

17. The electrocautery system of claim 12, wherein the electromagnetic coil comprises a plurality of coils connected in series or in parallel to at least one power source.

18. The electrocautery system of claim 12, wherein the electromagnet is further constructed to generate a magnetic field of sufficient orientation to switch the magnetically-switchable device off or into back-up mode.

19. The electrocautery system of claim 12, wherein the electromagnetic coil defines a hollow space therein.

20. The electrocautery system of claim 12, wherein the magnetic field generated by the electromagnet is at least 8 Gauss.

21. The electrocautery system of claim 12, further comprising a lock-out connected to the control circuit that is configured to shut off the electromagnet after a predetermined period of time to prevent the magnetically-switchable device from automatically reprogramming.

22. The electrocautery system of claim 21, wherein the predetermined period of time is approximately 10 seconds.

* * * * *